United States Patent
Delaage et al.

(10) Patent No.: US 8,383,069 B2
(45) Date of Patent: Feb. 26, 2013

(54) INCUBATION DEVICE FOR SEROLOGY AND HISTOLOGY SLIDES

(76) Inventors: Michel Delaage, Marseilles (FR); Gilles Nicolai, Six Fours (FR); Georges Szekeres, Pecs (HU)

( * ) Notice: Subject to any disclaimer, the term of this patent is extended or adjusted under 35 U.S.C. 154(b) by 1144 days.

(21) Appl. No.: 10/599,454

(22) PCT Filed: Mar. 30, 2005

(86) PCT No.: PCT/FR2005/000770
§ 371 (c)(1),
(2), (4) Date: Sep. 15, 2008

(87) PCT Pub. No.: WO2005/095575
PCT Pub. Date: Oct. 13, 2005

(65) Prior Publication Data
US 2009/0011425 A1   Jan. 8, 2009

(30) Foreign Application Priority Data
Mar. 31, 2004   (FR) ..................... 04 03365

(51) Int. Cl.
*B01L 9/00* (2006.01)

(52) U.S. Cl. ........................................ 422/563
(58) Field of Classification Search ............... None
See application file for complete search history.

(56) References Cited

U.S. PATENT DOCUMENTS

| | | | | |
|---|---|---|---|---|
| 4,974,952 A | * | 12/1990 | Focht | 359/398 |
| 5,414,556 A | * | 5/1995 | Focht | 359/398 |
| 5,583,043 A | * | 12/1996 | Sakariassen | 435/284.1 |
| 6,395,536 B2 | | 5/2002 | Freeman | 435/288.3 |
| 7,223,363 B2 | * | 5/2007 | McNeely et al. | 422/417 |
| 2003/0087292 A1 | * | 5/2003 | Chen et al. | 435/6 |
| 2004/0086428 A1 | * | 5/2004 | Loeffler et al. | 422/100 |

FOREIGN PATENT DOCUMENTS
WO   WO 00/63670   10/2000

* cited by examiner

*Primary Examiner* — Ann Lam
(74) *Attorney, Agent, or Firm* — Joseph G. Seeber

(57) ABSTRACT

This application relates to an incubation device for serology or histology supports. It also relates to any apparatus comprising one such device, and to the use of said apparatuses and/or devices in analysis or diagnosis methods.

35 Claims, 10 Drawing Sheets

Fig. 8A
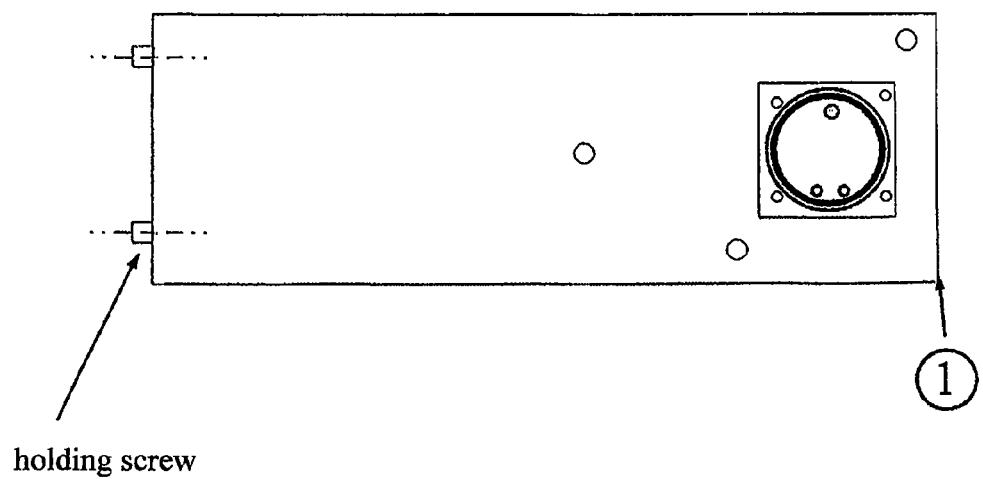
holding screw
Fig. 8B
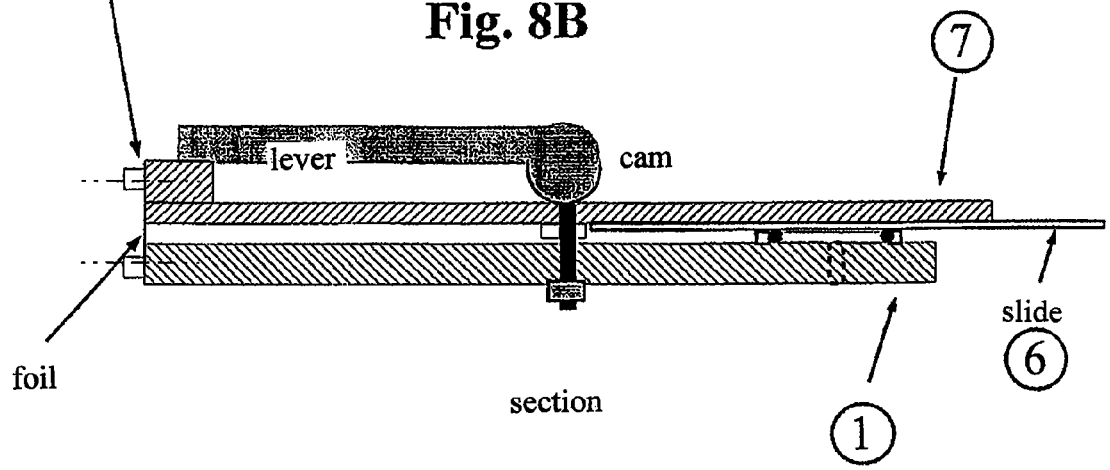
Figure 8

US 8,383,069 B2

INCUBATION DEVICE FOR SEROLOGY AND HISTOLOGY SLIDES

CROSS REFERENCE TO RELATED APPLICATIONS

This application is a national stage of PCT International Application No. PCT/FR2005/000770, filed on 30 Mar. 2005, and published in French on 13 Oct. 2005, as WO 2005/095575 A2, and claims priority to French Patent Application No. 04 03365 filed on 30 Mar. 2005, the entire disclosures of which are incorporated herein by reference.

This invention relates to an incubation device for serology and histology supports. It also relates to any apparatus comprising one such device, and to the use of said apparatuses and/or devices in analysis or diagnosis methods.

BACKGROUND TO THE INVENTION

Numerous diagnosis tests are based upon the reaction in heterogeneous phase between a level and solid surface (typically a microscope slide) and a liquid phase.

In a first variation (such as for example serological tests), the biological sample to be tested is contained in the liquid phase, and reacts with a slide carrying reactive elements, for example proteins, cells, DNA sequences, bacteria, viruses, etc. placed in advance on the slide. After a first reaction, the slide is placed in contact with a revealing reagent.

According to another variation, the biological sample to be tested is placed on the slide, the reactive (antibodies, DNA or RNA probes, etc.) and revealing elements then being in the liquid phase. This is the case for example with histological tests where the sample is a tissue section taken from the organism of a patient.

Nowadays, these different operations for manipulating the solid phase and the liquid phase are essentially manual. Certain reagents are placed directly on the slide or, in the serological mode, it is the biological sample itself, then the slide or slides are soaked in successive baths which implement the dying operations necessary for the observation. Various disadvantages result from this, and in particular:

a risk of faulty manipulation when a sample of several microliters is placed on a slide and can slide outside of the reactive zone, a lack of reproducibility because it is impossible to accurately control the shear stresses to which the deposit on the slide is subjected, a drift of the reagents which, for reasons of cost, are not renewed with each soaking.

The apparatuses currently available process the slides in the open with jets of liquid or baths, and this is associated with high consumption of reagent and a high risk of contamination. They are not adapted to random access use which alone is capable of responding to urgency. The apparatuses described for example in the patents or patent applications No. WO03/052386, U.S. Pat. No. 6,352,861 and U.S. Pat. No. 6,495,106 of LabVision, Ventana and BioGenex are of this type. They are adapted to immunohistology and are not used in serology.

There is therefore a real need for improved incubation devices for serology or histology slides which enable rapid, reliable and automated analysis. In the field of serology there is in particular an unsatisfied need for a random access slide incubator which can process a slide in short periods of time (typically in less than an hour) and respond to urgent diagnosis in the case of infectious diseases. This invention offers a solution to these needs.

SUMMARY OF THE INVENTION

This invention relates to a novel incubation device for serology or histology slides. It also relates to any apparatus comprising one such device, and to the use of said apparatuses and/or devices in analysis or diagnosis methods.

The object of this invention is in particular to provide an incubation device for serology or histology slides which avoids the disadvantages mentioned above, by guaranteeing that the reactive elements are placed in contact reliably and automatically.

A first object of the invention is found more particularly in an incubation device for serology or histology slides which have a reactive zone, characterised in that:

it comprises a solid support (1) having a level surface on its upper face in which at least one alveolus (2) is disposed, open on the surface of the support, the opening having an area greater than that of the reactive zone of the slide and smaller than that of the surface of the slide, the base of the alveolus has at least two orifices (4) allowing the circulation of fluid(s) in the alveolus, the contour of the opening of the alveolus is advantageously provided with means allowing to ensure a seal, preferably a join (5); and the device further comprises means for disposing and/or locking a serology or histology slide (6) such that the reactive zone of the slide is located in front of the opening of the alveolus on the surface of the support, the slide and the support thus co-operating in order to form a sealed incubation chamber.

In particularly preferred embodiments of the invention:

the device further comprises means to allow a supply of fluid(s) to the alveolus (or incubation chamber), and/or the support has a plurality of alveoli as defined above enabling the parallel incubation of several samples disposed on a same slide or on different slides, and/or the device further comprises automatic supply means for the slides, and possibly a read-out identifying the slides, and/or the device further comprises means for transferring the slide to a signal read-out device, and/or the base of the alveolus has three orifices, one for discharging fluids, one for the inflow of liquids, and one for the inflow of gases.

In a particularly advantageous manner, in the device of the invention, the object-carrying slide (6) forms the upper, removable surface of an incubation chamber, said chamber being sealed and being provided with orifices (4) which allow the circulation of the different fluids necessary for the development of serology or histology reactions. Thus in particular, according to the invention:

the sample (in serological mode) or the reagents (in histological mode) are not positioned on the slide, but directly in the device at a point intended for this purpose, the successive reagents are placed in contact with the slide by laminar scavenging strictly limiting shearing, the operations follow "with lost reagent"—after each reaction the reagent used (or the excess of reagent) is evacuated, and is not re-used.

These features are particularly advantageous and make it possible for the reactive elements to be placed in contact reliably and automatically, and to provide reproducible results.

Another object of the invention relates to a serological analysis method comprising the incubation of a serology slide including a reactive zone comprising a series of deposits of infectious, pathogenic, allergenic or autoantigenic agents with a sample of serum from a patient, or a dilution of the same, then the revelation of the antibodies of the sample fixed on the deposits by means of labelled reagents, characterised in that the incubation is implemented in a device as defined above. The sample to be tested can be introduced into an alveolus before the slide is positioned, then the slide is applied to the support surface such as to form the sealed incubation chamber in which the reactive zone of the slide is in contact with the sample. As a variation, the sample to be tested can be introduced (pumped) into the incubation chamber formed by the slide placed on the alveolus.

Another object of the invention relates to a histological analysis method comprising the incubation of a histological slide comprising a reactive zone comprising a tissue sample from a patient with a solution of specific antibodies, then the revelation of the antibodies of the solution fixed on the sample by means of labelled reagents, characterised in that the incubation is implemented in a device as defined above.

The invention also relates to the use of a device as defined above for serological or histological analysis.

Another aspect of the invention relates to kits, in particular for biological analysis, comprising a device as defined above.

The invention is applicable in numerous fields, in particular for histological or serological analysis in a medical, veterinary, environmental, agri-food context, etc.

DETAILED DESCRIPTION OF THE INVENTION

As indicated above, the invention relates to a device adapted to the analysis of serology or histology slides. The device advantageously comprises a solid support (1) having a level surface on its upper face in which at least one alveolus (2) is disposed, open on the surface of the support, the support co-operating with the surface of the slide in order to form, on the alveolus, a sealed incubation chamber of which the slide forms the upper, detachable surface, the base (i.e. the whole wall forming the alveolus) of the alveolus having moreover at least two orifices (4) which allow the circulation of fluid(s) (liquids, gases) in the incubation chamber formed in this way.

The support used can be of various shapes and dimensions, in so far as it comprises a level (flat) surface, preferably on the upper face. The support is typically rectangular in shape, adapted to the normal shape of the serology or histology slides, even though any other shape can be considered (square, circular, triangular, etc.). Thus, when the positioning of the slide is guaranteed by the cover, the alveolus support can be of a size limited to the contour of the surface which provides a seal, typically a join limiting the alveolus. The thickness of the support must be sufficient in order to make it possible to accommodate the alveolus (a cavity), of a volume appropriate for forming an incubation chamber. Typically, the incubation chamber (and so the alveolus) has a volume of between 5 and 500 µl, for example between 10 and 350 µl, and the support should have a thickness of greater than 3 mm, for example of between 0.5 and 3 cm.

The solid support can be made from a variety of materials, possibly mixed. In particular, it can be composed of (or based upon) plastic material, metal and/or any rigid material which is resistant to saline solutions and to temperatures greater than or equal to 37° C. In a preferred embodiment, the solid support is composed of (or based upon, i.e. comprises) polymethacrylate, polyester, polycarbonate, nylon (delrin, rilsan) or stainless steel, on their own or in mixtures.

The alveolus disposed in the support can adopt different shapes according to the applications intended and/or the type of support used. A priori, there is no specific restriction as regards the shape of the alveolus, provided that the opening has an area greater than that of the reactive zone of the slide and smaller than that of the surface of the slide so as to allow the incubation chamber to be formed. Moreover, as described in the text below, the support can comprise a plurality of alveoli which allow separate analysis of several samples. In preferred embodiment variations, the alveolus (and its opening) is circular or elongated in shape, with the largest possible radiuses of curvature. Of course other shapes can be considered (rectangular, elliptic, etc.).

On the other hand, as indicated above, the contour of the alveolus opening is preferably provided with a join (5) which makes it possible to guarantee that the incubation chamber is sealed. The join can be created for example in or from any flexible material, preferably latex, synthetic rubber or silicone. Furthermore, the join can be level or toric in form. It can have a variable diameter or thickness, typically of between 0.5 and 5 mm.

The orifices (4) provided in the base of the alveolus preferably have a small diameter because they are essentially intended to ensure the circulation of liquids and/or gases. Typically, their diameter is between 0.1 and 3 mm, preferably between 0.3 and 2 mm, and more preferably between 0.5 and 2 mm. In order to allow better circulation of the fluids in the incubation chamber, and in particular in order to provide scavenging, the orifices are advantageously disposed at either side of the alveolus, i.e. typically diametrically opposed. Thus, when the incubation chamber is formed by positioning the slide, the orifices are to be found disposed on either side of the reactive zone, and make it possible to implement scavenging of the latter.

In one preferred embodiment of the device of the invention, the alveolus has two diametrically opposed orifices, one for the inflow of fluids, and the other for the discharge of fluids.

Of course, additional orifices (for example 1 or 2) can be provided, either for supplying liquid(s), or for drying or for supplying gas, for example, or else for improving the flux or the scavenging within the incubation chamber. Thus, in one preferred embodiment of the device of the invention, the base of the alveolus comprises three orifices: one discharge orifice and two inflow orifices, one for liquids and the other for gases, in particular for the drying air. More preferably, in this embodiment the discharge orifice is disposed on one side of the base of the alveolus, and the two inflow orifices are disposed on the diametrically opposed side, typically close to one another (see FIG. 8A).

According to one particularly preferred embodiment of the invention, the device further comprises means for disposing and/or locking a serology or histology slide such that the reactive zone of the slide (6) is located in front of the opening of the alveolus on the surface of the support, the slide and the support thus co-operating in order to form a sealed incubation chamber.

The means making it possible to dispose and/or lock the slide on the support can be formed for a example by a counterbore, a shoulder or wedges. Such means make it possible to force correct positioning of the slide such that the reactive zone is located in front of the opening of the alveolus. In one preferred embodiment, a release (13) is provided in the support, at one end of the slide locator, so as to facilitate its release by simple pressure, and/or a moveable and articulated cover (7) makes it possible to lock the slide (support and hold) once in position.

In one particular variation, the means for positioning and/or locking the slide comprise an articulated frame (14), in particular with a slide, and possibly locking means. The articulated frame advantageously comprises an articulation or hinge which makes it possible to position the slide easily and with guidance (and thus to open and close the incubation chamber), and also, possibly, a cover (141). The locking means can comprise, for example, a toothed wheel (142) actuating a locking cam, or else an electromagnet.

In another particular embodiment, the means for positioning and/or locking the slide are formed by a fixed cover (7) provided with a locator (71) which enables the positioning of the slide (6), the support block of the alveolus being moveable in relation to said cover. In this case, it is the alveolus support which can be moved in a vertical direction such as to implement the closure of the incubation chamber when the slide is in place. In this variation, the slides are advantageously slid into a locator (71) (for example a groove) made in the cover, and the support elevation closes the incubation chamber (and places the reactive zone in contact with liquids previously or subsequently introduced into the latter). Preferably, in the device of the invention according to this embodiment, the support and the fixed cover are linked by means for guiding the movement of the support, and advantageously comprises means for controlling this movement which are, for example, electrical or mechanical. On the other hand, in this variation the cover is advantageously pierced by an opening (3) perpendicular to the incubation alveolus such as to allow the sample to be introduced into said alveolus before positioning the slide, should the occasion arise. FIG. 4 shows this arrangement from an isometric perspective.

Thus, one particular object of this invention relates to an incubation device for serology or histology slides which have a reactive zone, characterised in that it comprises:

- a solid, moveable support (1) having a level surface on its upper face in which at least one alveolus (2) is disposed, open on the surface of the support, the opening having an area greater than that of the reactive zone of the slide and smaller than that of the surface of the slide, in which the base of the alveolus has at least two orifices (4) allowing the circulation of fluid(s) in the alveolus, and the contour of the opening of the alveolus is provided with means which make it possible to ensure a seal;
- a fixed cover (7) provided with a locator (71) which makes it possible to position the slide, and an opening (3); and
- means for guiding the essentially vertical movement of the moveable support (1) towards the fixed cover (7) in order to make it possible to form a sealed incubation chamber between the alveolus and the slide when the latter is in position, the reactive zone of the slide being contained within said incubation chamber.

In one preferred embodiment, the guiding means for the vertical movement of the support comprise a hinge, preferably formed by a steel slide, placed sufficiently far away from the reactive zone of the slide when the latter is in position in order to guarantee substantially uniform pressure on the alveolus join, typically of at least 5, 6 or 7 cm, 10 cm for example, and fixed both to the cover and to the alveolus support (see FIG. 8B). The elevation of the support, of around 3 mm, can be performed manually, for example by means of a cam lever or mechanically by means of an electric motor or a jack.

In one preferred embodiment, the device of the invention further comprises means for the supply of fluid(s) to the incubation chamber. These supply means typically comprise at least one fluid supply reservoir (8) linked to a first orifice of the alveolus, called the inflow orifice, by a piping system for introducing fluid(s) into the alveolus, and a fluid recovery reservoir (9) linked to a second orifice of the alveolus, called the discharge orifice, by a piping system for eliminating fluids, said systems being connected to one or more pumps (10, 11).

In one variation of the embodiment, a single (preferably suction) pump is used to control the inflow and the discharge of the fluids.

In another embodiment, pressurisation of the reservoirs is used in order to move the fluids, and each supply channel is then provided not only with a valve, but also with a throughput regulation element such as a needle valve.

Advantageously, the device comprises several (for example 2 to 6) fluid supply reservoirs (8) linked to the inflow orifice, each reservoir being connected to a valve (12). The presence of several supply reservoirs makes it possible to introduce different reagents (liquids, gases) into the incubation chamber according to the adapted kinetics, doses and/or programmes. The presence of valves makes it possible to regulate individually the supply of each of the fluids (or from each of the supply reservoirs provided).

In a preferred variation, a peristaltic type pump is used, preferably with a reversible movement, guaranteeing the successive positioning of the liquids by suction, each liquid being under the control of a valve. The throughput of the pump can vary, for example between 0.1 and 10 ml/min. A syringe-type pump can be used with the same throughputs.

On the other hand, in a particular variation of the invention, the device further comprises an additional pump (11) for drying the slide or for cleaning the device. Advantageously, this is a non-volumetric air pump with a throughput of, for example, between 100 and 3000 ml/min. Of course these figures are provided for information, and some embodiments can stray from these limits and be adapted by an expert in the field.

The two pumps can be connected to the same discharge piping, each one being controlled by a valve. In the case of a peristaltic pump, the valve is not necessary. The air pump for drying can either be a suction pump, in which case it is connected on the same side as the suction pump for the liquids, or of the blower type, in which case it is connected on the other side (as shown by FIG. 5).

The valves used are advantageously controlled electrically. According to the embodiments, 3 to 6 valves control the arrival of the reagents, and 0 to 3 valves control the suction pumps. In a preferred embodiment, one of the valves is used in order to guarantee the atmospheric pressurisation, facilitating the opening and closure of the incubation chamber.

In a particular embodiment of the invention, the suction circuit can be switched directly to one or another of the fluid supply reservoirs (8) by a three-way valve (FIG. 9). The presence of this auxiliary circuit makes it possible to eliminate any bubbles which may be introduced into the system when a reservoir is changed or filled.

The device can be limited to a single slide but, in an advantageous embodiment, several slides are incubated in parallel. In this case, several alveoli are advantageously provided in the support (or several supports are used), each alveolus comprising its set of solenoid valves (12). In one particular embodiment, the solenoid valves are controlled synchronously, and a multi-channel peristaltic pump ensures the transfer of the reagents simultaneously into the different alveoli. An auxiliary contact can be provided in order to prevent the opening of valves on an unused alveolus.

Thus, a particular object of the invention is a device in which the support comprises a plurality of alveoli as defined above, allowing the incubation in parallel of several serology or histology slides. Typically, each alveolus is provided with fluid supply means, and the alveolus/supply system units thus formed are arranged to function in parallel, using the same fluids, according to synchronous or staggered sequences.

In a preferred embodiment of the invention, the liquid transfer pump is a suction pump, the air pump is a blower pump and connected to the inflow orifice of the alveolus such that the fluids still circulate in the same direction and are evacuated into a single receptacle (9).

In a particular embodiment, the device of the invention further comprises automatic slide feed means and, possibly, a read-out for identifying slides. The slide can be identified by a bar code or, preferably, by an electronic tag.

In another particular embodiment, which can be combined with any of the preceding ones, the device of the invention further comprises means for transferring a slide to a signal read-out device, in particular an optical read-out in order to make observations and to take measurements of the biological features of the samples. Advantageously, the signal read-out device is integrated into the support and/or the cover of the incubation device according to the invention.

In one particular embodiment of the invention, the material of the support is transparent and the base of the alveolus is polished such that the optical observation device can be integrated into the incubation device. As an example, one can provide the incubation device of FIG. 4 with fluorescence detection optics with an electroluminescent diode integrated into the support and a retractable objective coming into contact with the slide. Such optical devices are largely facilitated by providing optic fibre, as an expert in the field knows how to do, in order to resolve the problems of bulk.

In one particular embodiment of the invention, the base of the alveolus to the right of the reactive zone of the slide is formed by the level side of a plano-convex lens, the first lens of an objective for collecting light emitted by the sample. According to this embodiment, for the fluorescence measurements the exciter source is placed above the slide.

The devices according to the invention are adapted to any type of serology or histology slide. In this context, in the sense of this application, "slide" is understood as being any rigid object-carrying element which can be used for immobilising a biological deposit, thus delimiting a reactive zone. It can be for example a solid lamella, a membrane, a filter, etc. The slide can be made of (or based upon) any known and conventional material such as plastic, glass, nylon, ceramic, metal, biological polymers, silica, etc. Preferred slides are glass microscope slides. Their dimensions are generally standard, i.e. approximately 25 mm×75 mm. In a preferred embodiment the slides are provided with a fail-safe mechanism, for example in the form of a notch in a corner.

The automatic commercial pipetors, such as those produced by Cavro, Hamilton or Gilson, can be used in order to introduce the sample (serological version) or the monoclonal antibody (histological version) at the appropriate dilution.

Different embodiments and applications of the invention are described in the examples and in the attached figures in which.

Figure 1:
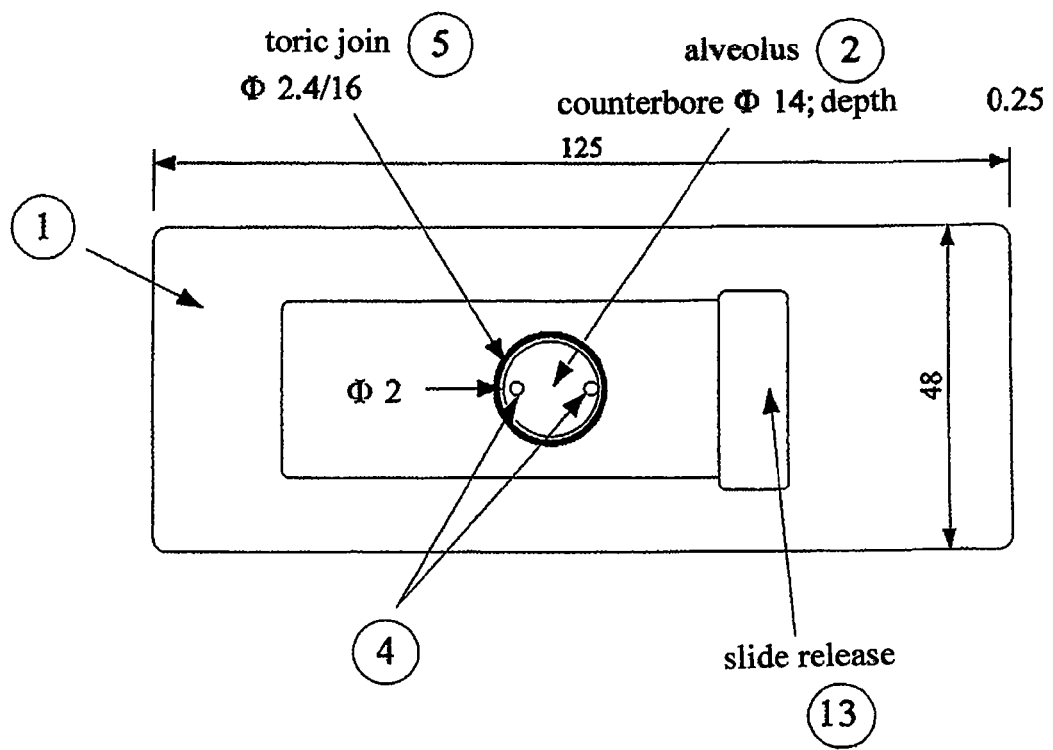
FIG. 1 is a top view of the serological version of the incubation alveolus. Dimensioned drawing. (1): hollowed support of the incubation alveolus (2) and a slide impression. (4): inflow and discharge orifices for liquids and gases. (5): sealing join. (13): slide release.
Figure 2:
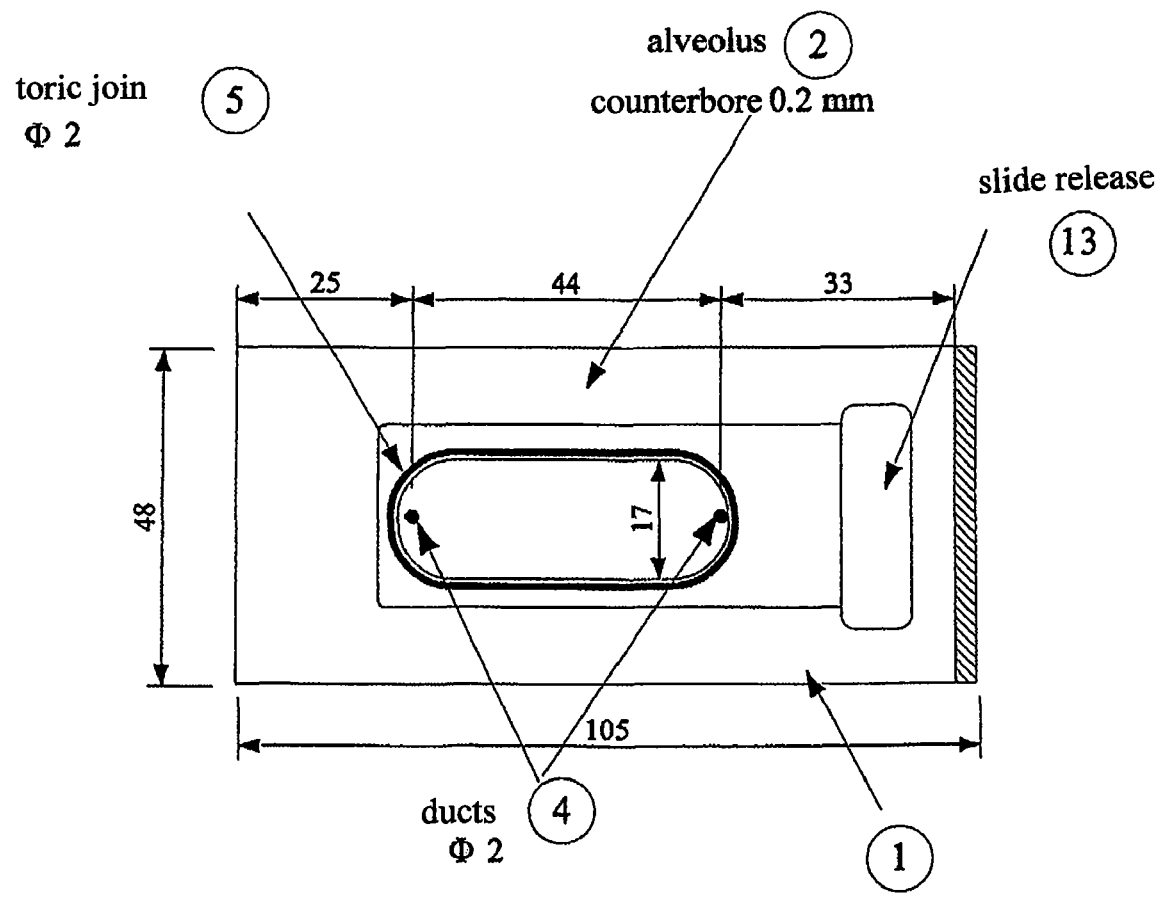
FIG. 2 is a top view of the histological version of the incubation alveolus. Dimensioned drawing.
Figure 3:
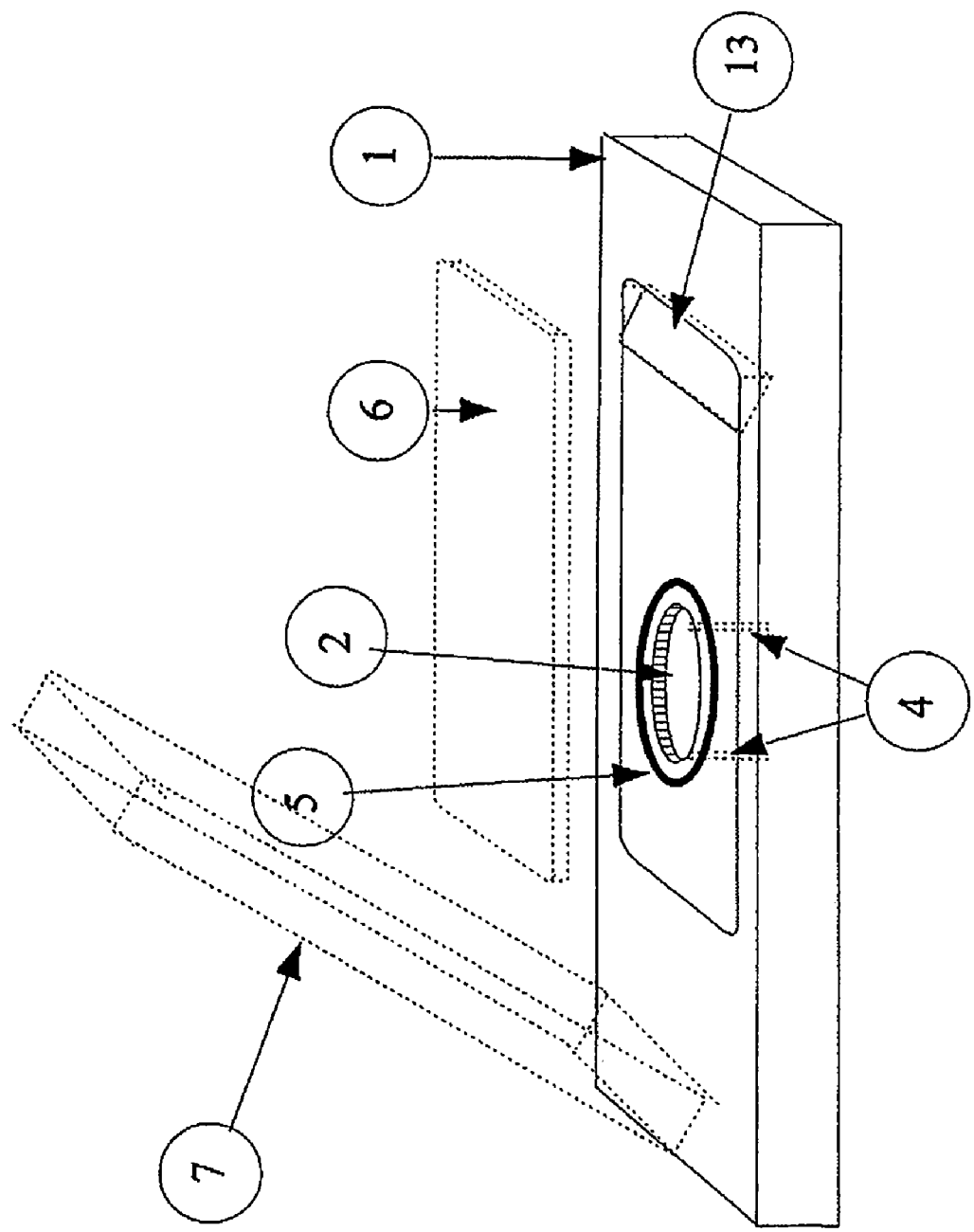
FIG. 3 shows a block carrying the incubation alveolus according to the invention with a fixed support and moveable cover. (1): hollowed support of the incubation alveolus (2) and a slide impression. (4): inflow and discharge orifices for liquids and gases. (5): sealing join. (6): slide, shown out of position. (7): cover, shown without the articulations. (13): slide release.
Figure 4:
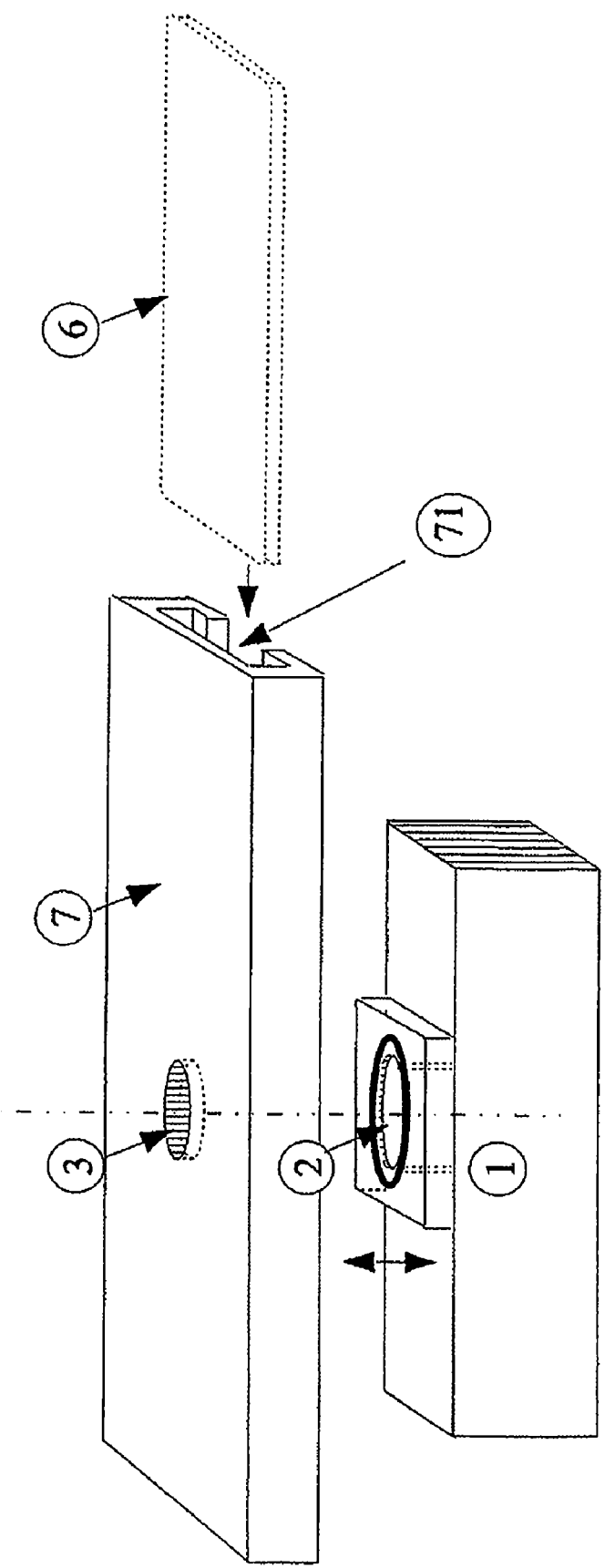
FIG. 4 shows a device according to the invention with a fixed cover (7) and a moveable alveolus support (1) provided with means for guiding and positioning the slide; (3) cover opening allowing the sample to be introduced into the alveolus. The mechanism for raising and lowering the block is not shown.
Figure 5:
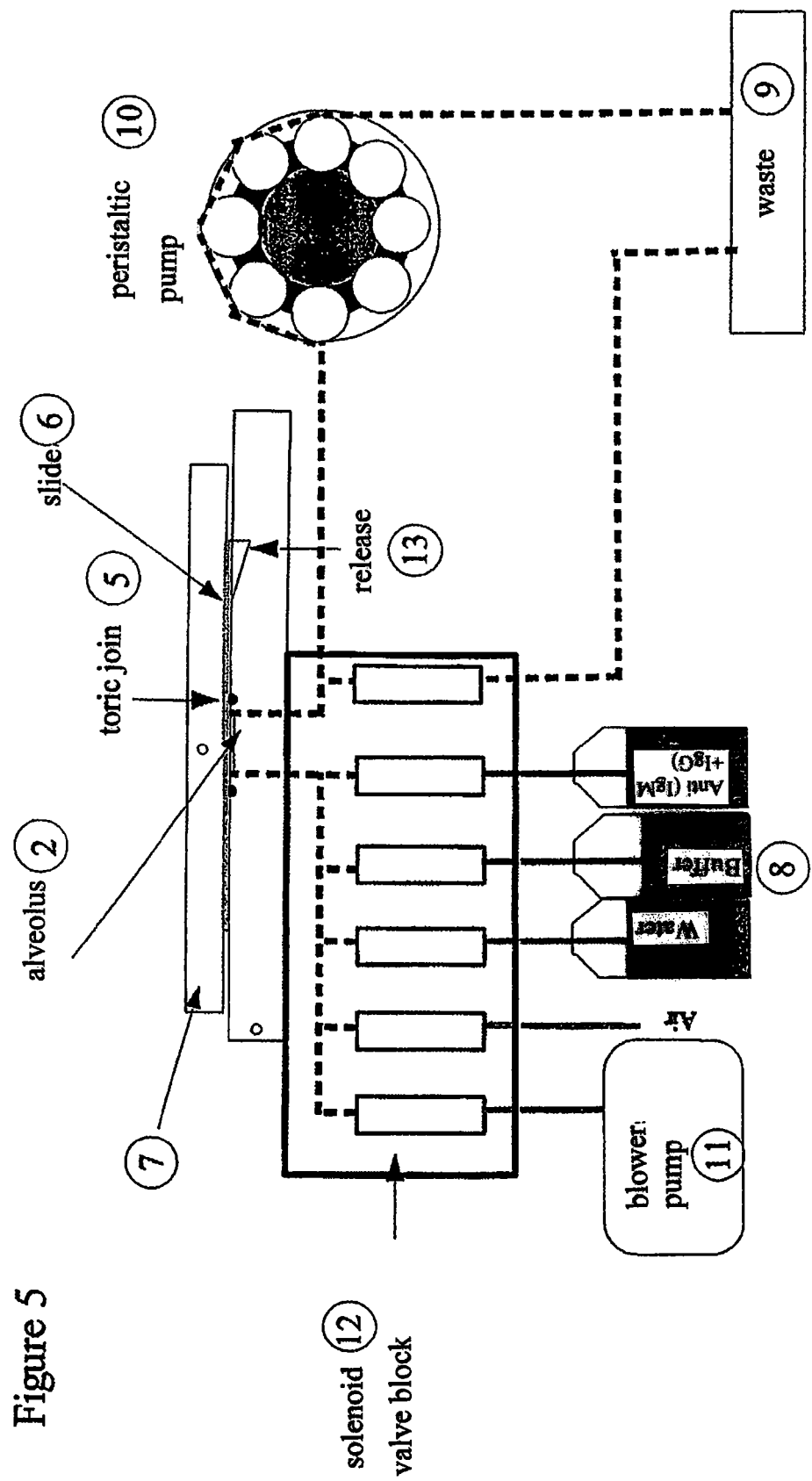

FIG. 5 shows a schematic section showing the circulation principle in the serological version. The solenoid valve block (12) is formed by a methacrylate pedestal pierced with fine channels and onto which the valves are bolted. The block itself is bolted onto the alveolus support. The piping is shown by dotted lines. The electric circuit is not shown.

Figure 6:
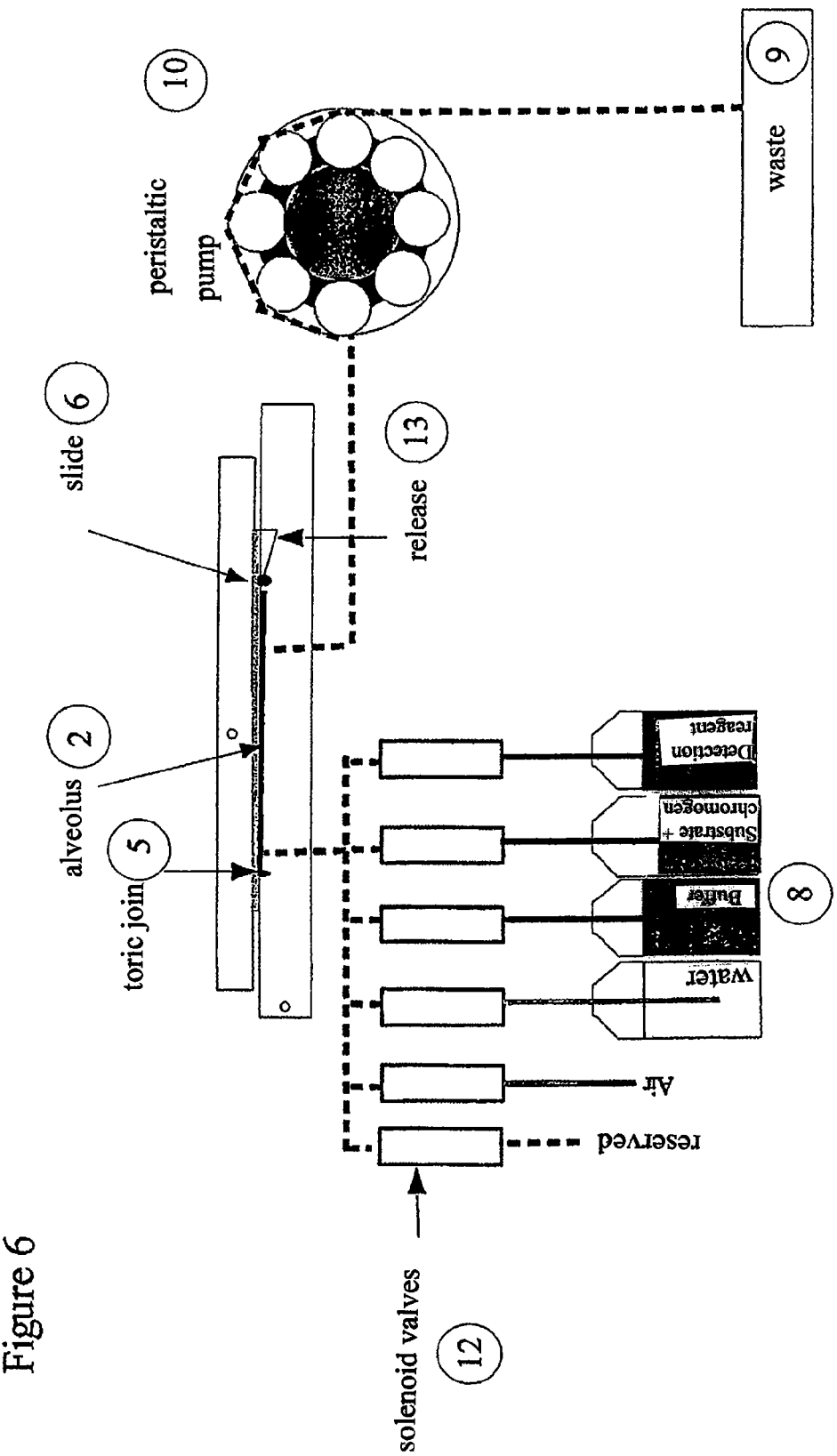

FIG. 6 is a diagram showing the circulation principle in the histological version. There is no drying device, as this is considered to be optional in histology.

Figure 7:
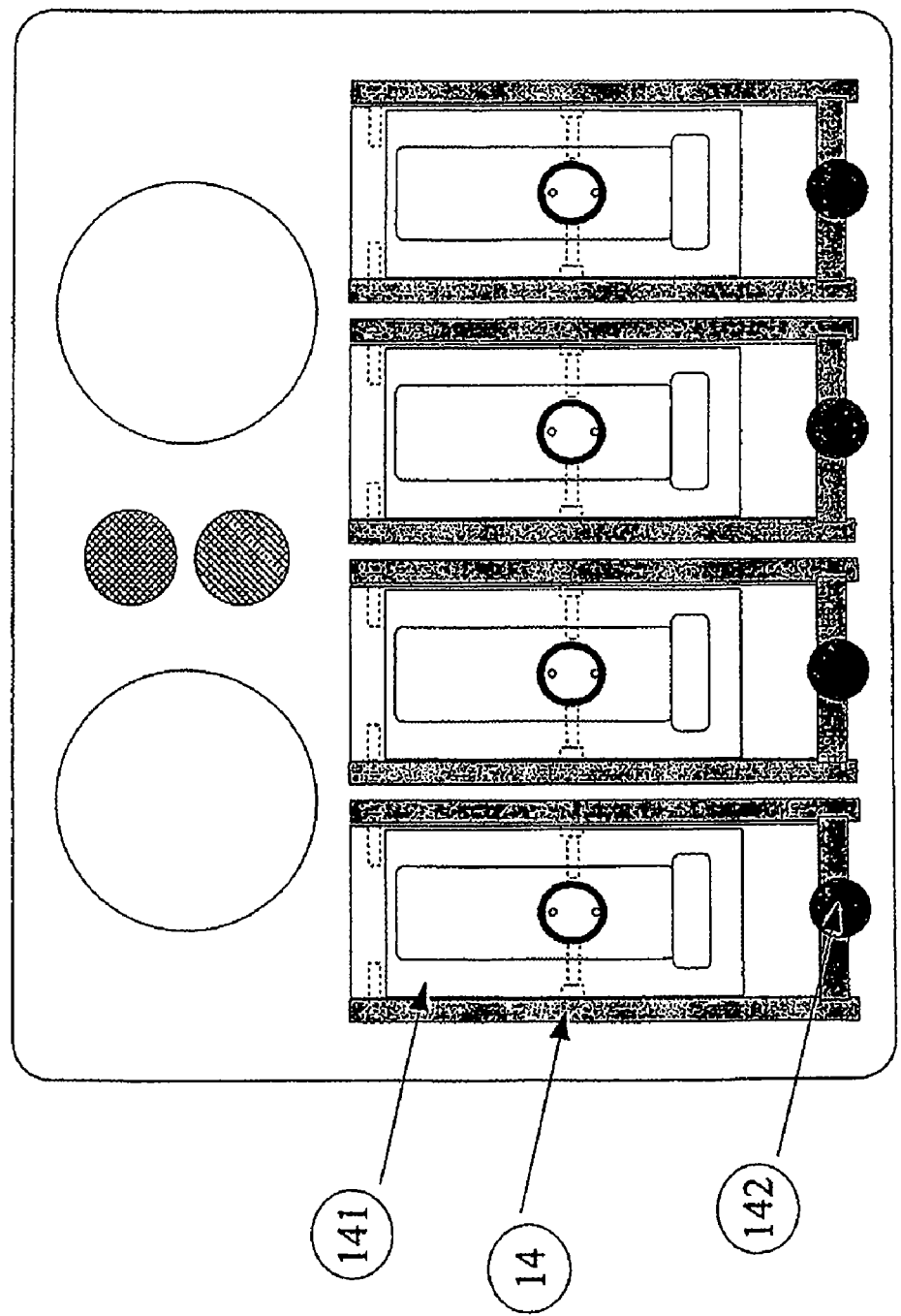

FIG. 7 shows an arrangement for an incubator with four slides according to the invention, in a top view in the scale 1/2—The slide locking devices are shown in grey. Each device comprises an articulated (metal) frame (14) supporting a transparent cover (141) and a toothed wheel (142) actuating the locking cam (not shown). The large circles are the locators for the buffer and water flasks, the small hatched circles are the locators for the restricted use reagents such as the dyed agents.

FIG. 8A shows a diagram of an alveolus with three orifices, two for the inflow of fluids, and one for their discharge; FIG. 8B shows a device according to the invention provided with means for guiding and for positioning the slide (6), formed by a hinge comprising a steel (foil) slide attached to the cover (7) and to the alveolus support (1). In this representation, the support elevation is implemented manually by a cam lever.

Figure 9:
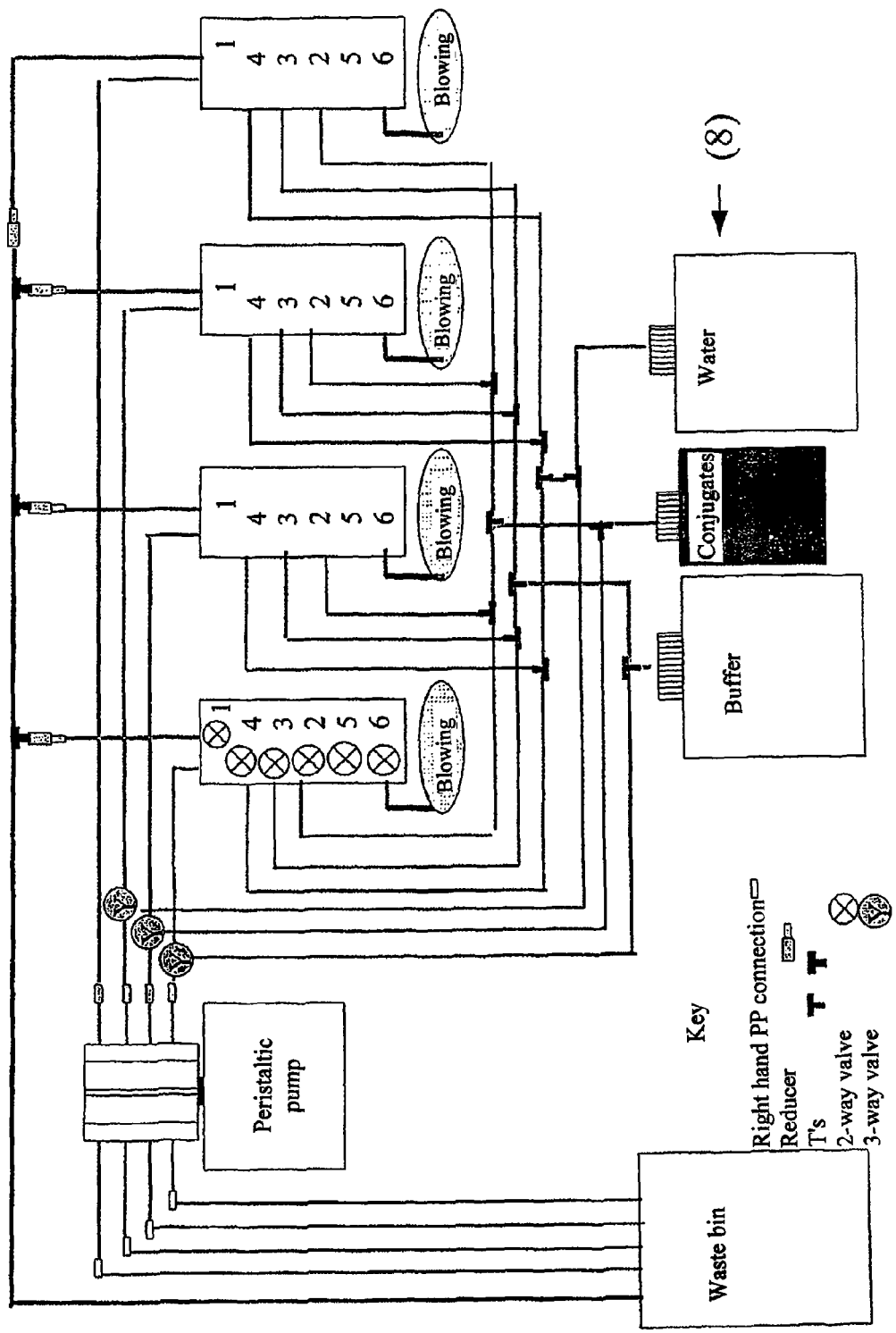

FIG. 9 shows a hydraulic elevation diagram (fluidic cabling) of a device of the invention comprising three-way valves (symbol Y) making it possible to switch a suction circuit directly to one or another liquid supply reservoir (8) by means of an auxiliary circuit.

Figure 10:
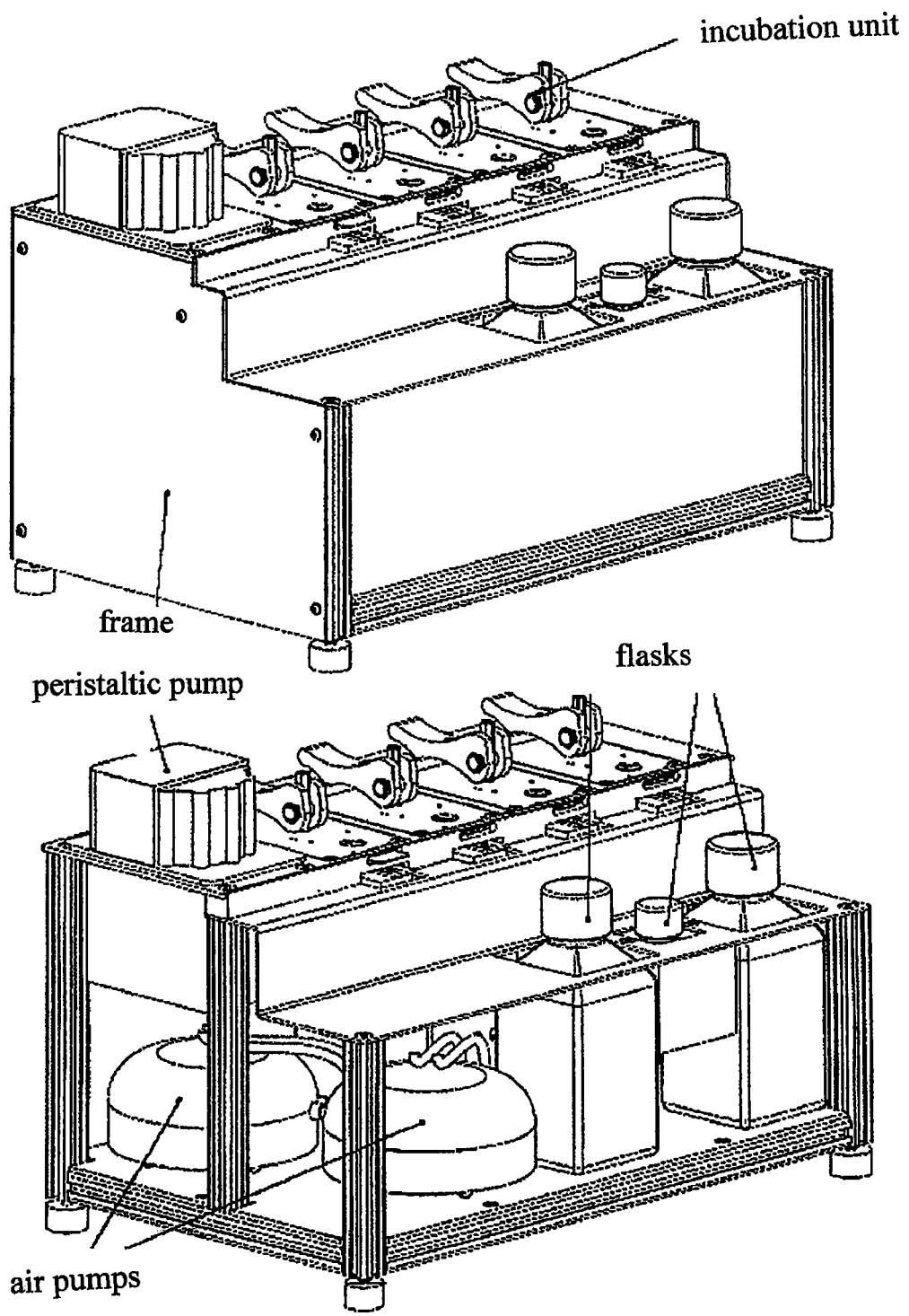

FIG. 10 shows an arrangement for an incubator with four slides according to the invention, seen from an isometric perspective. The incubation units correspond to the principle diagrams of FIG. 8.

As illustrated in the figures, the invention can be used for the analysis of serology slides. In the serological mode, the slide carries a series of biological deposits ("spots"), for example of infectious, pathogenic, autoantigenic or allergenic agents. The deposits are carefully identified, this identification constituting an identification code. The liquid sample to be tested is a patient serum, generally diluted in an appropriate buffer.

The reagents used are:

1) The agents revealing the patient's antibodies possibly fixed on the slide and, preferably, animal origin antibodies coupled with marker molecules, for example fluorescent molecules. The antibodies of animal origin (goat, mouse, rat, rabbit) are preferably of two types: some of them recognise M type immunoglobulins, the others G type immunoglobulins. Each type of antibody is coupled to a specific marker. For example, the first ones are coupled to fluorescein and the second ones to rhodamine. Of course other combinations of dyes and/or markers are possible such as the Alexa Fluor 488 and Alexa Fluor 594 fluorochromes, provided that the excitation or emission spectra are different. Such dyes and/or markers can be found commercially, for example with Sigma (Saint-Louis, Mo., USA), Molecular Probes (Eugene, Oreg., USA) or FluoProbes, including in a form conjugated with the anti IgG and anti IgM antibodies. In the invention they are preferably used in diluted mixtures such as to implement rapid and specific marking according to the procedures known to experts in the field.

2) The rinsing solutions which are used are slightly detergent saline solutions according to compositions known to experts in the field for rinsing the reagents in contact with the slide, and more astringent solutions and distilled water for rinsing the apparatus.

The incubations can be carried out at the temperature of the laboratory, or at 37° C. if an accelerating effect is desired. They take place in a series of phases: the first step is the positioning in the alveolus (2) or in the incubation chamber of the liquid sample to be tested, generally between 10 and 100 µl. The sample can be introduced automatically by means of the pumping system or, in a preferred embodiment, by pipetting into the open alveolus before the slide is applied. Next, the slide (6) is positioned, making sure that the reactive zone is placed in contact with the liquid sample to be tested. The slide is applied to the contour of the alveolus such as to create a seal. After an appropriate incubation time, the device rinses the slide using a rinsing solution, then introduces the marked revealing reagents (e.g., the fluorescent antibody conjugates). At the end of a new incubation, the incubation chamber is rinsed once again. In a preferred embodiment, the final operation is drying by air scavenging. During the automatic incubation process, the reagents are therefore successively introduced by pumping and come into contact with the reactive zone of the slide with pause times allowing the reaction-diffusion coupling. At the end of the process the slide is or is not dried by a flow of gas.

In order to guarantee a high level of sensitivity, each reaction must be as complete as possible, with the exception of the first one which can be "controlled by kinetics" in order to better reflect the differences between one patient and another. Furthermore, the invention makes it possible to be highly specific, i.e. in particular the absence of artefacts due to the persistence of the preceding reagent in the following incubation.

In a preferred embodiment, several alveolus/microscope slide/pumping system incubation units are associated in order to function in parallel according to synchronous or staggered sequences using reservoirs of common reagents.

The invention can also be implemented in order to analyse histology slides. In the histological mode, the slide carries a tissue sample from a patient which can be in the form of a quick frozen and dried section or of a deparaffinised section, for example. The reagents used in this embodiment are:

1) The specific antibody or antibodies recognising the elements of interest on the sample section. These antibodies are preferably monoclonal and they recognise either differentiation antigens such as cytokeratin or tumoral antigens such as the carcinoembryonic antigen. They can be directly marked or revealed by secondary antibodies, marked themselves, either by fluorescent molecules, or by enzymes.

3) The rinsing solutions which are used are slightly detergent saline solutions according to compositions known to experts in the field for rinsing the reagents in contact with the slide, and more astringent solutions and distilled water for rinsing the apparatus.

The incubations can be carried out at the temperature of the laboratory, or at 37° C. if an accelerating effect is desired. They take place in a series of phases: the first step is the positioning of the specific antibody which can be a monoclonal antibody appropriately diluted according to the rules known to experts in the field. The antibody can be introduced automatically using the pumping system, or in a preferred embodiment by pipetting into the open alveolus before the slide is applied. Several antibodies can be successively placed in contact with the slide by means of the incubator, provided that at the end the markings are distinguishable from one another. An expert in the field will have no trouble programming the appropriate sequence for making the marks which he has chosen. In one particular embodiment, drying by air scavenging is implemented in order to clean the apparatus after the slide has been removed.

In a preferred embodiment, several alveolus/microscope slide/pumping system incubation units are associated to function in parallel according to synchronous or staggered sequences, using reservoirs of common reagents.

Other aspects and advantages of this invention will become evident from reading the following examples of applications which must be considered as illustrative and not restrictive.

EXAMPLE 1

Description of a Serological Incubation

This embodiment is described in relation to FIG. No. 5.

Outside of the cell, the serum is heated for 30 minutes at 57° C. (decomplementation), then kept at 4° C.

Step 1—The serum is diluted to 1/100 in PBS milk (NaCl 0.15 M, phosphate pH 7 0;01 M, 50 ml+1.5 g of milk).

Step 2—40 µl of the sample (diluted serum) is introduced into the open chamber. The test slide (Inodiag) is placed over this, the spots in contact with the sample. The cell (incubation chamber) is closed and incubation takes place over 20 minutes.

Step 3—The "buffer" solenoid valve is then opened, and the suction pump (10) is actuated. Rinsing is implemented with 100 µl PBS buffer containing 0.05% Tween 20 for a period of approximately 30 seconds. This operation is implemented three times in succession.

Step 4—The "anti IgM+IgG" solenoid valve is then opened and the suction pump (10) actuated. This allows a mixture of anti IgG and anti IgM antibody (80 µl, diluted in PBS) to be introduced into the incubation chamber. Incubation takes place over approximately 10 minutes. This reagent is fluorescent. Next, rinsing identical to the previous step is implemented.

Step 5—The "water" solenoid valve is opened and the suction pump (10) is actuated for approximately 30 seconds.

Step 6—Finally, the solenoid valve linked to the air blower pump (11) is opened, as is the solenoid valve directly linked to the discharge reservoir (9). The air pump (11) is actuated for 20 seconds in order to dry the slide.

EXAMPLE 2

Description of a Histological Incubation

This embodiment is described more particularly in relation to FIG. No. 6.

Outside of the cell, the section is deparaffinised, rehydrated and pre-processed according to the rules of immuno-marking known to experts in the field.

Step 1—The sample (100 µl primary antibody (ref.: 10032.1, clone: B56, Histopathology, Pécs, Hungary) diluted to 1/100) is introduced into the open chamber.

Step 2—The microscope slide (6) (tissue section, 4 µ/m thick, human lymphatic ganglion) is placed over this, the section in contact with the diluted antibody. The cell (incubation chamber) is closed and incubation takes place over 20 minutes.

Step 3—The "buffer" solenoid valve is opened, and the suction pump (10) is actuated. Rinsing with 100 μl buffer, then wait for 3 minutes. This operation is implemented three times in succession.

Step 4—The "Detection reagent" solenoid valve is then opened, and the suction pump (10) is actuated. This allows detection reagent (100 μl, polymer conjugated with peroxidase enzyme) to be introduced into the incubation chamber. Incubation for 20 minutes.

Step 5—Next, rinsing identical to the previous step is implemented.

Step 6—The "chromogen substrate" solenoid valve is then opened, and the suction pump (10) is actuated. This makes it possible to introduce revealing reagent of a mixture of diaminobenzidine and oxygenated water (100 μl) into the incubation chamber. Incubation for 20 minutes.

Step 7—The "water" solenoid valve is opened, and the suction pump (10) is actuated. Distilled water is introduced in order to stop the enzymatic action.

The invention claimed is:

1. An incubation device for serology or histology slides having a reactive zone, wherein said device:
   comprises a solid support having a level surface on its upper face in which at least one alveolus is disposed, the alveolus having an opening on the surface of the support, the opening having an area greater than an area of the reactive zone of the slide and smaller than an area of a surface of the slide,
   a base of the alveolus has at least two orifices allowing circulation of fluid(s) in the alveolus,
   a contour of the opening of the alveolus is provided with means which make it possible to ensure a seal; and
   the device further comprises slide locator means for positioning and/or locking a serology or histology slide such that the reactive zone of the slide is located in front of the opening of the alveolus on the surface of the support, the slide and the support thus co-operating in order to form a sealed incubation chamber.

2. The device according to claim 1, wherein the slide locator means comprise a counterbore, and a shoulder or wedges.

3. The device according to claim 1 or 2, wherein a release is provided in the support, at one end of the slide locator means, so as to facilitate release of the slide by simple pressure.

4. The device according to claim 1, wherein the means for positioning and/or locking the slide comprise an articulated frame with a slide.

5. The device according to claim 4, wherein the articulated frame further comprises locking means.

6. The device according to claim 1, wherein the means for positioning and/or locking the slide comprise a fixed cover provided with a locator which enables the positioning of the slide, the support being moveable in relation to said cover.

7. The device according to claim 6, wherein the support and the fixed cover are linked by means for guiding movement of the support, and the device further comprises means for controlling said movement.

8. The device according to claim 7, wherein the means for controlling said movement comprises electric or mechanical means.

9. The device according to claim 6 or 7, wherein the fixed cover is pierced by an opening perpendicular to the alveolus.

10. The device according to claim 6, wherein said device comprises a signal read-out device integrated into the support and/or the cover.

11. The device according to claim 1, wherein the alveolus is circular or elongated in shape.

12. The device according to claim 1, wherein the alveolus has a volume of between 5 and 500 μl.

13. The device according to claim 1, wherein the means which make it possible to ensure a seal comprises a join.

14. The device according to claim 13, wherein the join is made from a flexible material, and/or is level or toric in form.

15. The device according to claim 14, wherein the flexible material comprises latex, synthetic rubber or silicone.

16. The device according to claim 1, wherein the solid support is made of plastic material, metal and/or any rigid material which is resistant to saline solutions and to temperatures greater than or equal to 37°.

17. The device according to claim 16, wherein the solid support is composed of polymethacrylate, polyester, polycarbonate, nylon (delrin, rilsan) or stainless steel, on their own or in mixtures.

18. The device according to claim 1, wherein the orifices of the alveolus have a diameter of between 0.1 and 3 mm and/or are disposed at either side of the alveolus such that scavenging can be implemented.

19. The device according to claim 18, wherein the alveolus has two diametrically opposed orifices, one for the inflow of fluids, and the other for the discharge of fluids.

20. The device according to claim 1 or 18, wherein the alveolus has three orifices, one for discharging fluids, and the two others, close to one another, for the inflow of liquids and gases respectively.

21. The device according to claim 1, wherein said device further comprises supply means for guaranteeing a supply of fluid(s) to the incubation chamber.

22. The device according to claim 21, wherein the supply means include at least one fluid supply reservoir linked to a first orifice of the alveolus, called the inflow orifice, by a piping system for introducing fluid(s) into the alveolus, and a fluid recovery reservoir linked to a second orifice of the alveolus, called the discharge orifice, by a piping system for eliminating fluids, said systems being connected to one or more pumps.

23. The device according to claim 22, wherein said device comprises several fluid supply reservoirs linked to the inflow orifice, each reservoir being connected to a valve.

24. The device according to claim 22 or 23, wherein the supply means comprise one or more three-way valve(s) which make it possible to switch a suction circuit directly to one or another liquid supply reservoir by means of an auxiliary circuit.

25. A device characterised in that the support has a plurality of alveoli as defined in claim 1.

26. The device according to claim 25, wherein each alveolus is provided with fluid supply means, and in that the alveolus/supply system units thus formed are arranged to function in parallel, using the same fluids, according to synchronous or staggered sequences.

27. The device according to claim 1, wherein said device further comprises automatic supply means for the slides, and.

28. The device according to claim 27, further comprising a readout identifying the slides.

29. The device according to claim 1, wherein said device further comprises means for transferring the slide to a signal read-out device.

30. A serological analysis method comprising incubation of a serology slide comprising a reactive zone having a series of deposits from infectious, pathogenic, allergenic or autoantigenic agents with a sample of serum from a patient, or a dilution of the same, then the revelation of the antibodies of the sample fixed on the deposits by means of labelled reagents, wherein the incubation is implemented in a device according to claim 1.

31. The method according to claim 30, wherein the sample is introduced into the alveolus before the slide is positioned, then the slide is applied to the surface of the support such as to form the sealed incubation chamber in which the reactive zone of the slide is in contact with the sample.

32. The method according to claim 30, wherein the sample is pumped into the incubation chamber formed by the slide positioned on the alveolus.

33. A histological analysis method comprising incubation of a histology slide comprising a reactive zone having a tissue sample from a patient with a solution of specific antibodies, then the revelation of the antibodies of the solution fixed on the sample by means of labelled reagents, wherein the incubation is implemented in a device according to claim 1.

34. A kit comprising a device according to claim 1.

35. An incubation device for serology or histology slides having a reactive zone, wherein said device comprises:
- a solid, moveable support having a level surface on its upper face in which at least one alveolus is disposed, the alveolus having an opening on the surface of the support, the opening having an area greater than an area of the reactive zone of the slide and smaller than an area of the surface of the slide, in which a base of the alveolus has at least two orifices allowing circulation of fluid(s) in the alveolus, and a contour of the opening of the alveolus is provided with means which make it possible to ensure a seal;
- a fixed cover provided with a locator which makes it possible to position the slide, and an opening; and
- means for guiding essentially vertical movement of the moveable support towards the fixed cover in order to make it possible to form a sealed incubation chamber between the alveolus and the slide when the slide is in position, the reactive zone of the slide being contained within said incubation chamber.

* * * * *